(12) United States Patent
Yao et al.

(10) Patent No.: US 12,338,430 B2
(45) Date of Patent: Jun. 24, 2025

(54) FILAMENTOUS FUNGUS AND USE THEREOF IN GAS METABOLISM

(71) Applicant: Northwest A&F University Shenzhen Research Inst, Shenzhen (CN)

(72) Inventors: Yiqing Yao, Shenzhen (CN); Caiyun Yang, Shenzhen (CN)

(73) Assignee: Northwest A&F University Shenzhen Research Inst, Shenzhen (CN)

( * ) Notice: Subject to any disclaimer, the term of this patent is extended or adjusted under 35 U.S.C. 154(b) by 0 days.

(21) Appl. No.: 18/934,153

(22) Filed: Oct. 31, 2024

(65) Prior Publication Data

US 2025/0163360 A1  May 22, 2025

(30) Foreign Application Priority Data

Nov. 20, 2023 (CN) .......................... 202311542973.3

(51) Int. Cl.
  *C12N 1/14*  (2006.01)
  *C12R 1/66*  (2006.01)
(52) U.S. Cl.
  CPC ............... *C12N 1/145* (2021.05); *C12N 1/14* (2013.01); *C12R 2001/66* (2021.05)
(58) Field of Classification Search
  CPC ........ C12N 1/145; C12N 1/14; C12R 2001/66
  See application file for complete search history.

(56) References Cited

FOREIGN PATENT DOCUMENTS

CN  117286037 B  3/2024

OTHER PUBLICATIONS

Techaoei et al., Saudi Journal of Biological Sciences, vol. 27, Issue 11, 2020, pp. 2883-2889, doi.org/10.1016/j.sjbs.2020.08.037. (Year: 2020).*
Office Action mailed on Jan. 2, 2024 for Chinese Patent Application No. 202311542973.3.
Notice of Allowance mailed on Feb. 6, 2024 for Chinese Patent Application No. 202311542973.3.

* cited by examiner

*Primary Examiner* — Kade Ariani
(74) *Attorney, Agent, or Firm* — Thomas Horstemeyer, LLP

(57) ABSTRACT

Disclosed is a filamentous fungus and use thereof in gas metabolism, which belongs to the technical field of microorganisms. The filamentous fungus is an *Aspergillus cejpii* strain S8 deposited in the China General Microbiological Culture Collection Center (CGMCC), No. 3, No. 1, West Beichen Road, Chaoyang District, Beijing on Sep. 20, 2023, with a deposit number of CGMCC NO. 40828.

3 Claims, 3 Drawing Sheets
Specification includes a Sequence Listing.

```
SEQUENCE LISTING

Sequence total quantity: 3
SEQ ID NO: 1               moltype = DNA    length = 533
FEATURE                    Location/Qualifiers
source                     1..533
                           mol_type = other DNA
                           note = 18S rDNA sequence of Aspergillus cejpii strain S8
                           organism = synthetic construct
SEQUENCE: 1
tgggccaccc tcccccgtg  tctaccgtac cttgttgctt cggcgggccc gccgcctgac   60
ggccgccggg gaggcctccg cgcccccggg cccgcgcccg ccgaagacgc ccacgtgaac  120
tctgccctga aggattgcag tctgagtcga ttatcataat cagttaaaac tttcaacaac  180
ggatctcttg gttccggcat cgatgaagaa cgcagcgaaa tgcgataact aatgtgaatt  240
gcagaattca gtgaatcatc gagtctttga acgcacattg cgcccctgg  tattccgggg  300
ggcatgcctg tccgagcgtc attgctgccc tcaagcacgg cttgtgtgtt gggccgccgt  360
ccccgcctcc ccggggacgg gcccgaaagg cagcggcggc accgcgtccg gtcctcgagc  420
gtatggggct tcgtcacccg ctctgcaggc ccggccggcg ccggccgacc accaacccac  480
ttcttaaggt tgacctcgga tcaggtaggg atacccgctg aacttaagca tat          533

SEQ ID NO: 2               moltype = DNA    length = 19
FEATURE                    Location/Qualifiers
source                     1..19
                           mol_type = other DNA
                           note = ITS1 primer sequence
                           organism = synthetic construct
SEQUENCE: 2
tccgtaggtg aacctgcgg                                                 19

SEQ ID NO: 3               moltype = DNA    length = 20
FEATURE                    Location/Qualifiers
source                     1..20
                           mol_type = other DNA
                           note = ITS4 primer sequence
                           organism = synthetic construct
SEQUENCE: 3
tcctccgctt attgatatgc                                                20
```

FILAMENTOUS FUNGUS AND USE THEREOF IN GAS METABOLISM

CROSS REFERENCE TO RELATED APPLICATION

This patent application claims the benefit and priority of Chinese Patent Application No. 202311542973.3 filed with the China National Intellectual Property Administration on Nov. 20, 2023, the disclosure of which is incorporated by reference herein in its entirety as part of the present application.

REFERENCE TO SEQUENCE LISTING

A computer readable XML file entitled "Sequence Listing", that was created on Oct. 14, 2024, with a file size of 4,666 bytes, contains the sequence listing for this application, has been filed with this application, and is hereby incorporated by reference in its entirety.

TECHNICAL FIELD

The present disclosure belongs to the technical field of microorganisms, and relates to a filamentous fungus and use thereof in gas metabolism.

BACKGROUND

Greenhouse gases are gases in the atmosphere that absorb solar radiation reflected from the earth's surface and re-emit the solar radiation, including water vapor, carbon dioxide, methane, and most refrigerants. Greenhouse gases have the ability to absorb infrared radiation and retain infrared heat. The increase of greenhouse gases can lead to an increase in the temperature of earth's surface, causing global climate changes, such as sea level rise and an increase in extreme climate events. The increase in greenhouse gases can also cause damage to ecosystems, such as ocean acidification, glacier melting, and loss of biodiversity.

Studies have found that microorganisms play an important role in decomposing and metabolizing greenhouse gases, which can further regulate ecosystems. Methane ($CH_4$), the primary gas produced by coal mine gas, coal seam gas, and garbage dumps, is flammable and explosive. It contributes about 15% to the greenhouse effect driving global climate change. Although the oxidation of atmospheric methane by methanotrophic bacteria accounts for only 5% to 15% of the global methane sink, this process is the only biological sink that consumes atmospheric methane and is of great significance for maintaining the balance of atmospheric methane concentration. Gas-fermenting bacteria are capable of decomposing and utilizing greenhouse gases, thereby reducing the damage caused by greenhouse gases to the ecosystem.

The process by which microorganisms decompose and metabolize greenhouse gases is characterized by its convenience and absence of toxic side effects. Therefore, it is of great significance to provide a strain capable of decomposing and metabolizing the greenhouse gases.

SUMMARY

In order to reduce the impact of greenhouse gases on the ecological environment, the present disclosure provides a filamentous fungus and use thereof in gas metabolism. The filamentous fungus is specifically an *Aspergillus cejpii* strain S8, which is capable of effectively utilizing methane ($CH_4$) and carbon dioxide ($CO_2$) as a carbon source and an energy source for its growth and reproduction, with a utilization rate of the $CH_4$ of 81.437% and a utilization rate of the $CO_2$ of 96.737%. The present disclosure provides a convenient method for the decomposition and metabolism of greenhouse gases without producing toxic by-products.

To achieve the technical purpose of the present disclosure, in one aspect, the present disclosure provides a filamentous fungus, specifically an *Aspergillus cejpii* strain S8.

In the present disclosure, the *Aspergillus cejpii* strain S8 is collected from a fermentation product of wheat straw provided by Northwest Agriculture & Forestry University after mesotemperature fermentation at 37° C. to produce methane. The preservation information is as follows:

taxonomic designation: *Aspergillus cejpii* S8;
  date of deposit: Sep. 20, 2023;
  full name of the depositary institution: China General Microbiological Culture Collection Center (CGMCC);
  address of the depository: No. 3, No. 1, West Beichen Road, Chaoyang District, Beijing;
  deposit number: CGMCC NO.40828.

Further, the *Aspergillus cejpii* strain S8 is obtained from the post-methane fermentation products through enrichment culture, screening, and purification. After morphological identification, it is found that the surface of the colony of the strain is white, widely spread in a cotton-like shape, and granular; the back of the colony is light yellow and spread radially to the surroundings. The spores of the strain are mainly produced by cell expansion and spore wall thickening, distributed at the top and side walls of aerial hyphae, and round in shape. The strain is identified as *Aspergillus cejpii* and named S8. The 18S rDNA sequence of *Aspergillus cejpii* strain S8 is set forth in SEQ ID NO: 1.

Further, the filamentous fungus is cultured in an inorganic salt medium at 28° C. and 170 rpm for 3 d with constant-temperature shaking. The inorganic salt medium includes: 0.5 g/L of $KH_2PO_4$, 0.5 g/L of $Na_2HPO_4$, 0.4 g/L of NaCl, 1.0 g/L of $KNO_3$, 0.5 g/L of $NH_4Cl$, 1.0 g/L of $MgSO_4·7H_2O$, 0.2 g/L of $CaCl_2$, 0.004 g/L of $FeSO_4·7H_2O$, 0.004 g/L of $CuSO_4·5H_2O$, 0.004 g/L of $MnSO_4·H_2O$, 0.004 g/L of $ZnSO_4·7H_2O$, and 0.00024 g/L of $NaMoO_4·2H_2O$.

Further, the filamentous fungus uses a greenhouse gas as energy to allow growth and reproduction, and the greenhouse gas includes $CH_4$ and $CO_2$.

In the present disclosure, an experiment on the utilization of methane and $CO_2$ by *Aspergillus cejpii* strain S8 has showed that the *Aspergillus cejpii* strain S8 has a $CH_4$ gas utilization rate of 81.437%, a volume utilization rate of 41.110%, and a mycelium dry weight of 36.433 mg, indicating that the *Aspergillus cejpii* strain S8 can utilize $CH_4$ as a carbon source and an energy source to allow growth and reproduction. The *Aspergillus cejpii* strain S8 has a $CO_2$ gas utilization rate of 96.737%, a volume utilization rate of 71.106%, and a mycelium dry weight of 43.367 mg, indicating that the *Aspergillus cejpii* strain S8 can utilize $CO_2$ as a carbon source and an energy source to allow growth and reproduction.

In another aspect, the present disclosure provides use of the filamentous fungus in absorption and metabolism of a gas. Further, the gas includes $CH_4$ and $CO_2$.

In another aspect, the present disclosure provides a microbial inoculant, including the *Aspergillus cejpii* strain S8. The *Aspergillus cejpii* strain S8 is used in absorption and metabolism of a gas, including $CH_4$ and $CO_2$.

The present disclosure further provides a method for absorbing and metabolizing a gas, including absorbing and metabolizing of the gas with *Aspergillus cejpii* strain S8, or preparing the *Aspergillus cejpii* strain S8 into a microbial inoculant to allow absorption and metabolism of the gas, where the gas includes $CH_4$ and $CO_2$.

Compared with the prior art, the technical solutions provided by the present disclosure at least have the following beneficial effects or advantages:

In the present disclosure, the filamentous fungus *Aspergillus cejpii* S8 can grow and reproduce using greenhouse gases as an energy source. Through the experiment on the utilization of gas by *Aspergillus cejpii* strain S8, it is found that this strain has a desirable utilization effect on methane gas. When *Aspergillus cejpii* strain S8 is added to pure methane gas, it is found that the utilization rate of $CH_4$ gas is significant, with the $CH_4$ gas utilization rate of 81.437%, the volume utilization rate of 41.110%, and the mycelium dry weight of 36.433 mg. The gas utilization rate by *Aspergillus cejpii* strain S8 in pure methane gas is 37.772 times that of the control group, the volume utilization rate is 14.809 times that of the control group, and the mycelium dry weight is 1.194 times that of the control group.

The results of the experiment on the utilization of gas by *Aspergillus cejpii* strain S8 shows that this strain has a desirable utilization effect on $CO_2$ gas. When the *Aspergillus cejpii* strain S8 is added to pure $CO_2$ gas, it can efficiently utilize $CO_2$ gas as the carbon source and the energy source required for growth and reproduction. The utilization rate of $CO_2$ gas by the strain is 96.737%, the volume utilization rate is 71.106%, and the mycelium dry weight is 43.367 mg. The gas utilization rate by *Aspergillus cejpii* strain S8 in pure methane gas is 40.731 times that of the control group, the volume utilization rate is 24.984 times that of the control group, and the mycelium dry weight is 1.509 times that of the control group.

In the present disclosure, the filamentous fungus *Aspergillus cejpii* S8 can better utilize $CH_4$ and $CO_2$. The strain can be used to reduce the emission of greenhouse gases such as $CH_4$ and $CO_2$, and can also be used in the treatment of methane gas. The filamentous fungus *Aspergillus cejpii* S8 can efficiently remove polluted gases in multiple scenarios and multiple sites; the prepared microbial inoculant can be recycled and reused after being used and treated, and has the characteristics of desirable removal effect, convenient use, no toxic by-products, and high environmental safety.

BRIEF DESCRIPTION OF THE DRAWINGS

In order to illustrate the examples of the present disclosure or the technical solutions in the prior art more clearly, a brief introduction of the accompanying drawings needed in the description of the examples or the prior art will be provided below. Obviously, the accompanying drawings in the following description are merely some examples of the present disclosure.

FIG. 1 shows a plate culture image of the *Aspergillus cejpii* strain S8 and a microscopic image of hyphae with spores; where

DETAILED DESCRIPTION OF THE EMBODIMENTS

The technical solutions of the present disclosure will be described in detail below in conjunction with specific examples, but the protection scope of the present disclosure is not limited to the examples. The experimental methods described in the following examples are conventional methods unless otherwise specified; and the reagents and materials can be obtained from commercial sources unless otherwise specified.

The inorganic salt medium includes: 0.5 g/L of $KH_2PO_4$, 0.5 g/L of $Na_2HPO_4$, 0.4 g/L of NaCl, 1.0 g/L of $KNO_3$, 0.5 g/L of $NH_4Cl$, 1.0 g/L of $MgSO_4 \cdot 7H_2O$, 0.2 g/L of $CaCl_2$, 0.004 g/L of $FeSO_4 \cdot 7H_2O$, 0.004 g/L of $CuSO_4 \cdot 5H_2O$, 0.004 g/L of $MnSO_4 \cdot H_2O$, 0.004 g/L of $ZnSO_4 \cdot 7H_2O$, and 0.00024 g/L of $NaMoO_4 \cdot 2H_2O$.

PDA medium includes: 200 g/L of potato, 20 g/L of glucose, 5 g/L of peptone, 3 g/L of potassium dihydrogen phosphate, 1.5 g/L of magnesium sulfate, and 20 g/L of agar.

The fermentation product after methanogenesis is provided by Northwest Agriculture & Forestry University, specifically a fermentation product after methanogenesis at 37° C. using wheat straw as a fermentation material.

Example 1

In this example, the screening and identification of *Aspergillus cejpii* strain S8 are provided.
1. Strain Screening 50 mL of inorganic salt medium was added into a 250 mL sealed bottle, the headspace gas in the sealed bottle was replaced with nitrogen, pure $CH_4$ was added into the sealed bottle, 0.5 g of methanogenic fermentation product was inoculated into each sealed bottle, and cultured at a constant temperature of 28° C. and 170 rpm with shaking, and an enriched culture was obtained after 3 days. 1 mL of the enriched culture was transferred to a new inorganic salt medium and the culture was continued at 28° C. and 170 rpm. 1 mL of the enriched culture was transferred to a new inorganic salt medium every 3 days and the culture was continued at 28° C. and 170 rpm. The transfer was repeated until the inorganic salt medium solution became turbid to obtain an enriched solution of efficient gas utilization strains. 2% agar powder was added to a inorganic salt medium to prepare an inorganic salt solid medium. The enriched solution of efficient gas utilization strains was serially diluted, spread on the inorganic salt solid medium and cultured in a 28° C. constant-temperature incubator. Single colonies with desirable growth were selected, purified, and stored in a 4° C. refrigerator for later use.

2. Morphological Identification of Strain

Figure 1A:
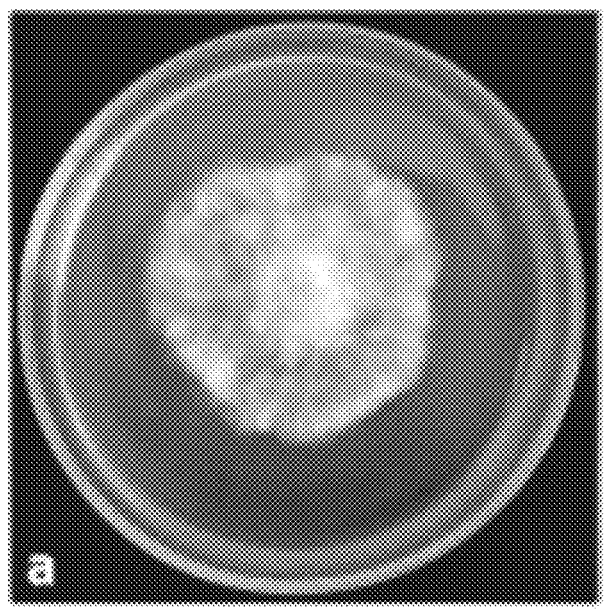
FIG. 1A is the front side of the plate culture image of *Aspergillus cejpii* strain S8.
Figure 1B:
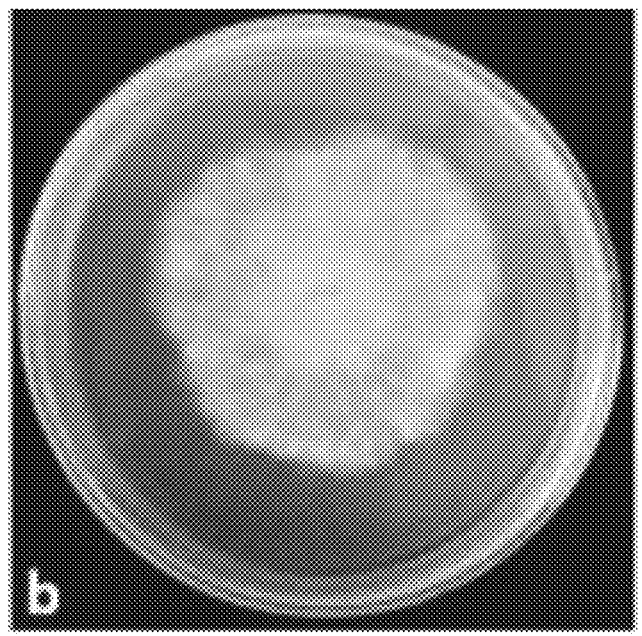
FIG. 1B is the back side of the plate culture image of *Aspergillus cejpii* strain S8.
Figure 1C:
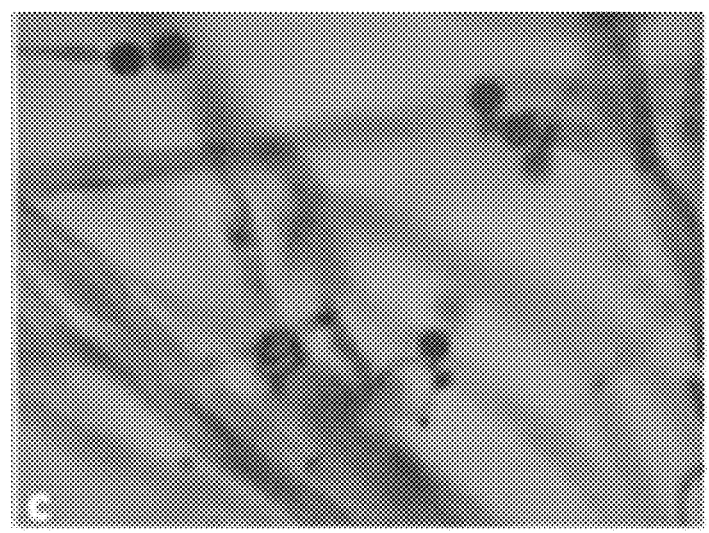
FIG. 1C is the microscope image of the hyphae with spores of *Aspergillus cejpii* strain S8.

The purified strain was inoculated on PDA medium and cultured at 28° C. for 7 days, the morphological characteristics and growth of the colonies were observed to understand the size and morphology of the mycelium (FIG. 1A and FIG. 1B). 1 to 2 drops of lactophenol cotton blue staining solution were dripped on a clean glass slide, a limited number of hyphae with spores were picked up with a dissecting needle and placed in the staining solution, and the hyphae were spread out, covered with a coverslip, and observed under a 40× optical microscope (FIG. 1C).

As shown in FIG. 1, the surface of the colony of the strain was white, widely spread in a cotton-like shape, and granular; the back of the colony was light yellow and spread radially to the surroundings. The spores of the strain are mainly produced by cell expansion and spore wall thickening, distributed at the top and side walls of aerial hyphae, and round in shape.

2. Molecular Identification of Strain

The PCR product of 18S rDNA was amplified using ITS1 and ITS4 regions, where the ITS1 primer had the sequence TCCGTAGGTGAACCTGCGG (SEQ ID NO: 2), and the ITS4 primer had the sequence TCCTCCGCTTATTGA-TATGC (SEQ ID NO: 3). 3 μL of PCR product was analyzed using 1.0% agarose gel electrophoresis. After confirming the single target band, the PCR product was purified and then sent to BGI Group (Shenzhen) for sequencing analysis. The 18S rDNA sequence of *Aspergillus cejpii* strain S8 was obtained as shown in SEQ ID NO: 1, with a length of 533 bp. The sequencing results were subjected to NCBI-BLAST sequence alignment, and the gene sequences of strains with higher homology were downloaded using MEGA7.0 software. The phylogenetic tree of this strain was constructed by the NJ method (FIG. 2).

Figure 2:
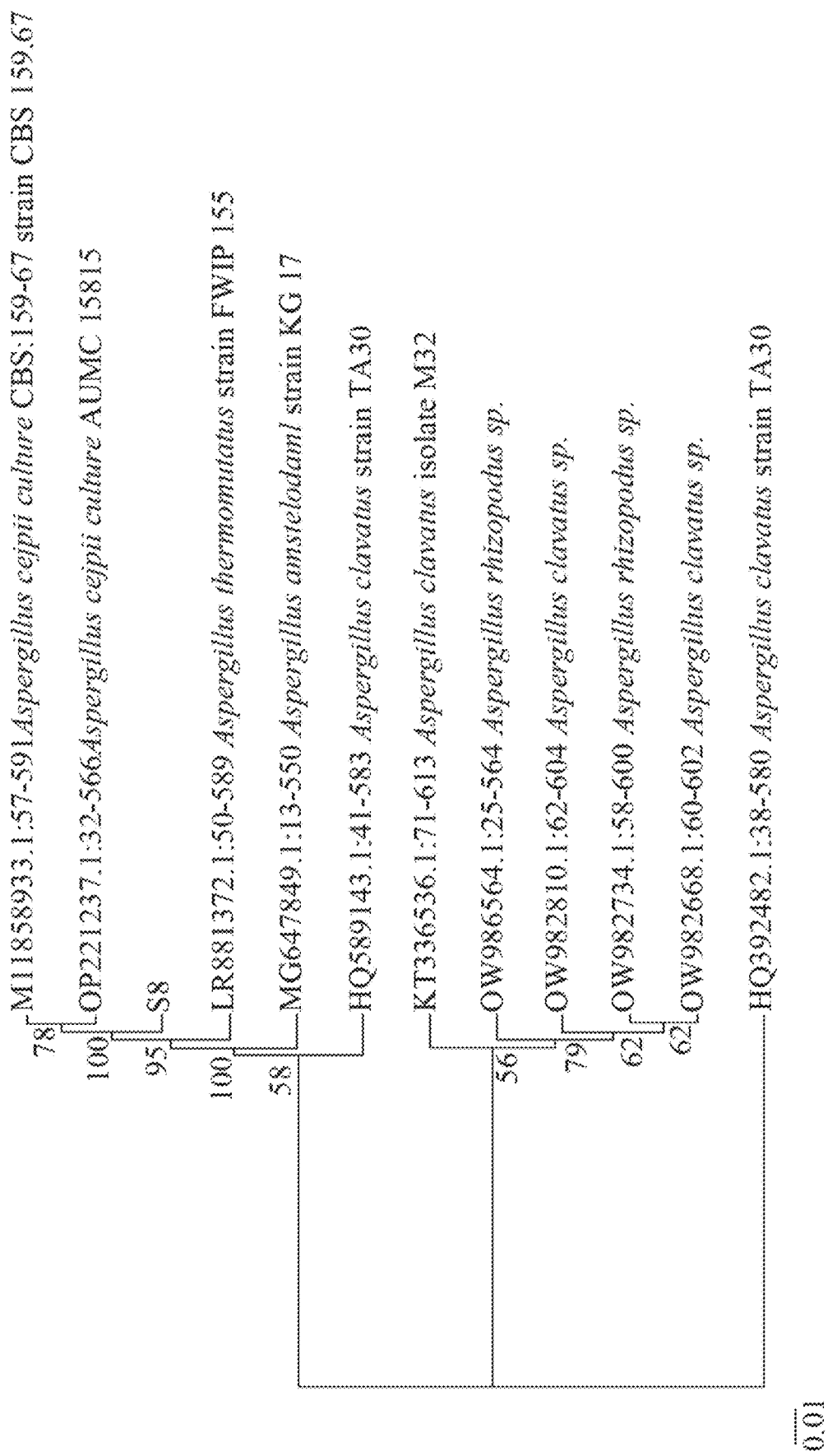
FIG. 2 shows the phylogenetic tree of the *Aspergillus cejpii* strain S8.

As shown in FIG. 2, the strain had a homology of up to 99.81% with *Aspergillus cejpii*. The phylogenetic tree results showed that the strain was located in the same branch with a bootstrap value of 100%. All branches had bootstrap values higher than 50%. Combining the morphological and molecular biological results, the strain was identified as *Aspergillus cejpii* and named S8.

Example 2

In this example, a test on the utilization effect of *Aspergillus cejpii* strain S8 on methane gas was provided.

50 mL of inorganic salt medium was added into a sealed bottle of 250 mL, the headspace gas in the sealed bottle was replaced with nitrogen, pure $CH_4$ was added into the sealed bottle, 2% of the isolated and purified fungal suspension of *Aspergillus cejpii* strain S8 was inoculated into each sealed bottle, while ambient air was added into a control group bottle as the control group. After 7 days of static culture at 28° C., the utilization rate of $CH_4$ by *Aspergillus cejpii* strain S8 was determined using a gas chromatography-mass spectrometer (GC2014C, purchased from Shimadzu Corporation), and the results were shown in Table 1. The test conditions were: TCD detector, inlet temperature 100° C., detector temperature 100° C., furnace temperature 90° C., argon as carrier gas, and the flow rate of 30 mL/min.

The volume utilization rate was determined by the water displacement gas collection method, and the results were shown in Table 1. To determine the mycelium dry weight, a filter paper was first dried to a constant weight, and the filter paper was accurately weighed. After a fermentation broth of the *Aspergillus cejpii* strain S8 was fully mixed, 30 mL of the fermentation broth was accurately measured for suction filtration, and an obtained filter residue was fully washed several times with distilled water until the filtrate was colorless, and then placed in a 55° C. constant-temperature drying oven to dry to a constant weight, a total mass of the filter residue and filter paper was accurately weighed. The measurement results were shown in Table 1. The formula for calculating the mycelium dry weight was: mycelium dry weight (mg)=total mass of filter residue and filter paper (mg)—mass of filter paper (mg).

TABLE 1

| Utilization effect of *Aspergillus cejpii* strain S8 on $CH_4$ | | | |
| --- | --- | --- | --- |
| Indicator | Gas utilization rate (%) | Volume utilization rate (%) | Mycelium dry weight (mg) |
| Control group | 2.156 | 2.776 | 30.512 |
| Treatment group | 81.437 | 41.110 | 36.433 |

As shown in Table 1, after adding *Aspergillus cejpii* strain S8 to the sealed bottle, the gas utilization rate of the ambient air was 2.156%, the volume utilization rate was 2.776%, and the mycelium dry weight was 30.512 mg. When the *Aspergillus cejpii* strain S8 was added to pure methane gas, the $CH_4$ gas utilization ability was relatively significant, and a large amount of $CH_4$ could be consumed as a carbon source and an energy source to allow growth and reproduction. The $CH_4$ gas utilization rate by the strain was 81.437%, the volume utilization rate was 41.110%, and the mycelium dry weight was 36.433 mg. The gas utilization rate by the *Aspergillus cejpii* strain S8 in pure methane gas was 37.772 times that of the control group, the volume utilization rate was 14.809 times that of the control group, and the mycelium dry weight was 1.194 times that of the control group. This indicated that the *Aspergillus cejpii* strain S8 had a desirable $CH_4$ gas utilization effect, showed high $CH_4$ gas utilization rate, and could use $CH_4$ as the carbon source and the energy source to allow growth and reproduction.

Example 3

In this example, a test on the utilization effect of *Aspergillus cejpii* strain S8 on $CO_2$ gas was provided.

50 mL of inorganic salt medium was added into a sealed bottle of 250 mL, the headspace gas in the sealed bottle was replaced with nitrogen, pure $CO_2$ was added into the sealed bottle, 2% of the isolated and purified fungal suspension of *Aspergillus cejpii* strain S8 was inoculated into each sealed bottle, while ambient air was added into a control group bottle as the control group. After 7 days of static culture at 28° C., the utilization rate of $CO_2$ by *Aspergillus cejpii* strain S8 was determined using a gas chromatography-mass spectrometer (GC2014C, purchased from Shimadzu Corporation), and the results were shown in Table 2. The test was carried out under the same conditions as in Example 2. The volume utilization rate was determined by the water displacement gas collection method, and the results were shown in Table 2. The mycelium dry weight was determined in the same manner as that in Example 2, and the results were shown in Table 2.

TABLE 2

| Utilization effect of *Aspergillus cejpii* strain S8 on $CO_2$ | | | |
| --- | --- | --- | --- |
| Indicator | Gas utilization rate (%) | Volume utilization rate (%) | Mycelium dry weight (mg) |
| Control group | 2.375 | 2.846 | 28.734 |
| Treatment group | 96.737 | 71.106 | 43.367 |

As shown in Table 2, after adding *Aspergillus cejpii* strain S8 to the sealed bottle, the gas utilization rate of the ambient air was only 2.375%, the volume utilization rate was 2.846%, and the mycelium dry weight was 28.734 mg. When *Aspergillus cejpii* strain S8 was added to pure $CO_2$, the $CO_2$ utilization ability was significant. The strain could efficiently utilize $CO_2$ as the carbon source and the energy source to allow growth and reproduction, with the $CO_2$ gas utilization rate of 96.737%, the volume utilization rate of 71.106%, and the mycelium dry weight of 43.367 mg. The gas utilization rate by *Aspergillus cejpii* strain S8 in pure $CO_2$ was 40.731 times that of the control group, the volume utilization rate was 24.984 times that of the control group, and the mycelium dry weight was 1.509 times that of the control group in pure $CO_2$. This indicated that the *Aspergillus cejpii* strain S8 had a desirable $CO_2$ gas utilization effect, showed high $CO_2$ gas utilization rate, and could use $CO_2$ as the carbon source and the energy source to allow growth and reproduction.

The described examples are merely some rather than all of the examples of the present disclosure. The detailed description examples of the present disclosure are not intended to limit the protection scope of the present disclosure, but merely to indicate selected examples of the present disclosure. All other examples obtained by a person of ordinary skill in the art based on the examples of the present disclosure without creative efforts shall fall within the protection scope of the present disclosure.

What is claimed is:

1. A method for absorbing and metabolizing a gas, comprising placing a filamentous fungus in an atmosphere of the gas to allow the strain to absorb and metabolize the gas as an energy source;

wherein the filamentous fungus is *Aspergillus cejpii* strain S8 and wherein the gas is $CH_4$, $CO_2$, or both; and wherein *Aspergillus cejpii* strain S8 is deposited in the China General Microbiological Culture Collection Center (CGMCC), No. 3, No. 1, West Beichen Road, Chaoyang District, Beijing on Sep. 20, 2023, with a deposit number of CGMCC NO. 40828 and the 18S rDNA sequence of *Aspergillus cejpii* strain S8 is set forth in SEQ ID NO: 1.

2. The method according to claim 1, wherein the *Aspergillus cejpii* strain S8 according to claim 1 is prepared into a microbial inoculant to allow absorption and metabolism of the gas.

3. The method according to claim 1, wherein the filamentous fungus is obtained through culturing in the following conditions:

an inorganic salt medium at 28° C. and 170 rpm for 3 days with constant-temperature shaking; and the inorganic salt medium comprises: 0.5 g/L of $KH_2PO_4$, 0.5 g/L of $Na_2HPO_4$, 0.4 g/L of NaCl, 1.0 g/L of $KNO_3$, 0.5 g/L of $NH_4Cl$, 1.0 g/L of $MgSO_4 \cdot 7H_2O$, 0.2 g/L of $CaCl_2$, 0.004 g/L of $FeSO_4 \cdot 7H_2O$, 0.004 g/L of $CuSO_4 \cdot 5H_2O$, 0.004 g/L of $MnSO_4 \cdot H_2O$, 0.004 g/L of $ZnSO_4 \cdot 7H_2O$, and 0.00024 g/L of $NaMoO_4 \cdot 2H_2O$.

* * * * *